United States Patent [19]

Meier et al.

[11] Patent Number: 5,563,271
[45] Date of Patent: Oct. 8, 1996

[54] N-(2-SULFATOETHYL)PIPERAZINE SULFATE AND ITS PREPARATION

[75] Inventors: Michael Meier, Frankfurt am Main; Heinz-Georg Kautz, Birstein; Andreas Schrell, Frankfurt am Main, all of Germany

[73] Assignee: Hoechst AG., Germany

[21] Appl. No.: 405,383

[22] Filed: Mar. 15, 1995

Related U.S. Application Data

[63] Continuation of Ser. No. 154,254, Nov. 18, 1993, abandoned.

[30] Foreign Application Priority Data

Nov. 21, 1992 [DE] Germany .................. 42 39 182.2

[51] Int. Cl.⁶ ............................................. C07D 295/108
[52] U.S. Cl. ............................................. 544/398; 544/401
[58] Field of Search ............................................. 544/398

[56] References Cited

U.S. PATENT DOCUMENTS 3,194,826  7/1965  Goldstein ................... 558/29

FOREIGN PATENT DOCUMENTS 238227   2/1960  Australia ................... 558/29
0546476  6/1993  European Pat. Off. .

OTHER PUBLICATIONS

Tomalia et al, J. Het. Chem. 9, pp. 891–894 (1972).
*Organic Functional Group Preparations* by Stanley R. Sandler and Wolf Karo, vol. III pp. 116–124, (1972).
Research Techniques in Organic Chemistry by Robert B. Bates and John P. Schaefer, pp. 50, 51, 55 (1971).
J. Amer. Chem. Soc., Bd. 75, 1953, "The Synthesis and Alkaline Decomposition of gamma–Amino–propylsulfuric Acid", pp. 2505–2506.
J. Amer. Chem. Soc., Bd. 57, 1935, "The Preparation of Ethylene Imine from Monoethanolamine", p. 2328.

*Primary Examiner*—Emily Bernhardt
*Attorney, Agent, or Firm*—Connolly & Hutz

[57] ABSTRACT

Preparation of N-(2-sulfatoethyl)piperazine sulfate by reacting N-(2-hydroxyethyl)piperazine in a mixture of high- or relatively high-percentage sulfuric acid and oleum or chlorosulfonic acid at temperatures of about 80° C. to about 250° C., introducing the sulfation mixture formed into a water-miscible aliphatic alcohol and isolating the N-(2-sulfatoethyl)piperazine sulfate formed.

17 Claims, No Drawings

N-(2-SULFATOETHYL)PIPERAZINE SULFATE AND ITS PREPARATION

This is a continuation of application Ser. No. 08/154,254, filed Nov. 18, 1993, now abandoned.

The invention relates to N-(2-sulfatoethyl)piperazine sulfate and processes for its preparation by reacting N-(2-hydroxyethyl) piperazine in mixtures of highly or relatively highly concentrated sulfuric acid and oleum or chlorosulfonic acid, dissolving the resulting reaction mixture in a lower alkanol, followed by isolation.

N-(2-Sulfatoethyl)piperazine sulfate is new and can be used as an agent for pretreating and modifying fiber materials, such as synthetic polyamide or polyurethane fiber materials, wool, silk or cellulose fiber materials, for subsequent dyeing with anionic dyes [Patent Application P 4,140, 410.6 ] which corresponds to U.S. application Ser. No. 07/984,977 which also corresponds to EP 546,476 EP 546 476 describes a process for the dyeing of fiber materials with water soluble anionic dyes which using a fiber material pretreated and modified by the compounds containing ester and amino groups. As examples for compounds containing ester- and aminogroups are described: N-(β-Sulfatoethyl)piperazine, N-[β-(β'-sulfatoethoxy)-ethyl]-piperazine, N-(γ-sulfato-β-hydroxypropyl)-piperidine, 2,3-disulfato-1-aminopropane. For the preparation of these ester compounds the reaction of the corresponding hydroxyalkylamines with fuming sulfuric acid is described. The work-up procedure comprises the reaction with calcium carbonate, filtration of the formed calcium sulfate and precipitation of calcium ions which are still present with sodium oxalate. After filtration of the calcium oxalate the aqueous solution of the product is evaporated to dryness.

The invention provides a process for preparing N-(2-sulfatoethyl)piperazine sulfate in high yield and high purity which is economical and easy to carry out in industry by reacting N-(2-hydroxyethyl)piperazine in a mixture of a high- or relatively high-percentage, preferably about 95 to 100%, particularly preferably 100%, sulfuric acid, and oleum (solution of sulfur trioxide in 100% sulfuric acid) or chlorosulfonic acid at temperatures of about 80° to about 250° C., preferably about 100° to about 170° C., introducing the resulting mixture into a water-miscible aliphatic alcohol, preferably methanol, ethanol or propanol, and isolating the N-(2-sulfatoethyl)piperazine sulfate formed.

In an advantageous embodiment, N-(2-hydroxyethyl)piperazine is esterified in a mixture of 100% sulfuric acid and oleum containing a stoichiometric amount of sulfur trioxide or in a mixture of relatively high percentage, for example about 95 to about 98%, sulfuric acid and chlorosulfonic acid at temperatures of about 80 to about 250° C., preferably about 100° to about 170° C. The sulfation mixture is then introduced into an aqueous, lower alkanol ($C_1$–$C_3$), preferably methanol or ethanol, and the N-(2-sulfatoethyl)piperazine sulfate is isolated and dried.

In the process according to the invention it is advantageous to use about 0.8 to about 3, preferably about 1.3 to about 1.7, parts by weight of 100% sulfuric acid per part by weight of N-(2-hydroxyethyl)piperazine. Larger amounts of sulfuric acid can also be used. However, this does not result in better quality and only increases the amounts of sulfuric acid to be disposed of. Instead of 100% sulfuric acid, sulfuric acid of lower concentration, for example 95 to 99% sulfuric acid, such as 96% sulfuric acid, can also be used. In accordance with the amount of water additionally present, more sulfur trioxide (in the oleum) or chlorosulfonic acid must be used in these cases.

When a mixture of 100% sulfuric acid and oleum is used sulfur trioxide is used in an amount of about 0.3 to about 0.8, preferably about 0.4 to about 0.7, particularly preferably about 0.55 to about 0.65, parts by weight per part by weight of N-(2-hydroxyethyl)piperazine. When a mixture of relatively highly concentrated sulfuric acid and chlorosulfonic acid is used, the chlorosulfonic acid is used in an amount of about 0.6 to about 1.3, preferably about 0.7 to about 1.0, particularly preferably about 0.80 to about 0.95, part by weight per part by weight of N-(2-hydroxethyl)piperazine.

The amount of the aqueous methanol or ethanol preferably used for precipitating N-(2-sulfatoethyl)piperazine sulfate is about 2.0 to about 6.0, preferably about 3.0 to about 5.0, particularly preferably about 3.2 to about 3.8, parts by weight per part by weight of N-(2-hydroxyethyl)piperazine. The water content of the alcohol should be between about 10 and about 30, preferably between about 15 and about 25, % by weight. Precipitation is started at a temperature of about 45° C. and then completed by cooling to about 15 to about 25° C. until crystallization is complete. For crystallization, about 0.005 to about 10, preferably about 0.01 to about 5, and particularly preferably about 0.05 to about 1, part by weight of N-(2-sulfatoethyl)piperazine sulfate are added to the precipitation mixture per 130 parts by weight of N-(2-hydroxyethyl)piperazine. However, larger amounts of seed crystals can also be added.

After precipitation, the N-(2-sulfatoethyl)piperazine sulfate is isolated and dried. It can then be used in that state.

Advantageously, the remaining lower aliphatic alcohol containing sulfuric acid is recovered by redistillation in vacuo and reused in a subsequent batch.

The examples which follow serve to illustrate the process according to the invention without limiting it thereto.

EXAMPLE 1

A 1 l four-necked flask equipped with stirrer, dropping funnel, thermometer and reflux condenser was charged with 400.0 g of 100% sulfuric acid, and 260.4 g (2.0 mol) of N-(2-hydroxyethyl)piperazine are added over a period of about 20 minutes at such a rate that the temperature does not exceed 150° C. This is followed by immediate addition of 246.2 g of 65% oleum also at such a rate that 150° C. are not exceeded. The reaction mixture (906 g) is transferred to a dropping funnel and about ⅓ in 890 g of 80% ethanol is then metered in at such a rate that the temperature does not exceed 45° C. The mixture is then cooled to about 20° C. with stirring, 0.1 g of N-(2-sulfatoethyl)piperazine sulfate is added, if necessary, as seed crystals, and the resulting mixture is vigorously stirred until the product precipitates in crystalline form. The remaining reaction mixture is then run in over a period of 10 minutes at such a rate that the temperature does not exceed 30° C. The mixture is then cooled to 20° C. with stirring and filtered off with suction. The product is washed with 900 g of 96% ethanol. Drying at 70° C. and 100 mbar gives 608.3 g of N-(2-sulfatoethyl)piperazine sulfate, which corresponds to a yield of 98.7% of theory. M.p.: 162° C. (phase transition?), 305° C. (decomposition) Calculated for $C_6H_{16}O_8N_2S_2$.

| Calculated for $C_6H_{16}O_8N_2S_2$ | | | |
|---|---|---|---|
| C 23.2% | H 5.2% | N 9.0% | S 20.6% |
| C 23.2% | H 5.2% | N 9.2% | S 20.2% |

$^1$H NMR ($d^6$-DMSO): δ=3.34–3.56 (m; 10H), 4.06–4.12 (m; 2H), 8.6–9.2 (broad, 4H)

EXAMPLE 2

A 1 l four-necked flask equipped with stirrer, dropping funnel, thermometer and reflux condenser was charged with 400.0 g of 100% sulfuric acid, and 260.4 g (2.0 mol) of N-(2-hydroxyethyl)piperazine are added over a period of about 20 minutes at such a rate that the temperature does not exceed 150° C. This is followed by immediate addition of 246.2 g of 65% oleum also at such a rate that 150° C. are not exceeded. The reaction mixture (906 g) is transferred to a dropping funnel and about ⅓ in 890 g of 80% ethanol is then metered in at such a rate that the temperature does not exceed 45° C. The mixture is then cooled to about 20° C. with stirring, 0.1 g of N-(2-sulfatoethyl)piperazine sulfate is added, if necessary, as seed crystals, and the resulting mixture is vigorously stirred until the product precipitates in crystalline form. The remaining reaction mixture is then run in over a period of 10 minutes at such a rate that the temperature does not exceed 30° C. The mixture is then cooled to 20° C. with stirring and filtered off with suction. The product is washed with 900 g of 96% ethanol. Drying at 70° C. and 100 mbar gives 604.9 g of N-(2-sulfatoethyl)piperazine sulfate, which corresponds to a yield of 98.1% of theory. The spectroscopic data are identical to those given in Example 1.

EXAMPLE 3

A 1 l four-necked flask equipped with stirrer, dropping funnel, thermometer, reflux condenser and gas introduction tube is charged with 206.3 g of 96% sulfuric acid and 130.2 g (1.0 mol) of N-(2-hydroxyethyl)piperazine over a period of about 20 minutes at such a rate that the temperature does not exceed 150° C. 169.9 g of chlorosulfonic acid are then metered in at 120° C. over a period of 1 hour with heating. During this addition, a vigorous stream of nitrogen is continuously introduced because of foaming of the reaction mixture (evolution of HCl). After addition is complete, the mixture is additionally stirred at 150° C. while introducing nitrogen until no more hydrogen chloride can be detected in the off-gas (about 1.5 h). The reaction mixture (446.9 g) is transferred to a dropping funnel and about ⅓ thereof in 447 g of 80% ethanol is then metered in at such a rate that the temperature does not exceed 45° C. The reaction is then continued as described in Example 1 to give 305.3 g of N-(2-sulfatoethyl)piperazine sulfate, which corresponds to a yield of 99.0% of theory.

The spectroscopic data and the melting point are identical to those given in Example 1.

EXAMPLE 4

A 1 l four-necked flask equipped with stirrer, dropping funnel, thermometer and reflux condenser was charged with 200 g of 100% sulfuric acid, and 130.2 g (1.0 mol) of N-(2-hydroxyethyl)piperazine are added over a period of about 20 minutes at such a rate that the temperature does not exceed 200° C. 123.1 g of 65% oleum are then metered in over 1 hour at such a rate that the temperature does not exceed 200° C. The reaction mixture (453.2 g) is transferred to a dropping funnel and about ⅓ in 453 g of 80% methanol is then metered in at such a rate that the temperature does not exceed 45° C. The mixture is then cooled to about 25° C. with stirring, 0.1 g of N-(2-sulfatoethyl)piperazine sulfate is added, if necessary, as seed crystals, and the resulting mixture is vigorously stirred until the product precipitates in crystalline form. The remaining reaction mixture is then run in over a period of 10 minutes at such a rate that the temperature does not exceed 25° C. Stirring at 25° C. is then continued for another 30 minutes, and the mixture is filtered off with suction. The product is washed with 412 g of methanol. Drying gives 303.7 g of N-(2-sulfatoethyl)piperazine sulfate, which corresponds to a yield of 98.5% of theory.

The spectroscopic data are identical to those given in Example 1.

What is claimed is:

1. N-(2-Sulfatoethyl)piperazine sulfate.

2. A process for preparing N-(2-sulfatoethyl)-piperazine sulfate, which comprises reacting N-(2-hydroxyethyl)piperazine in a mixture of about 0.8 to about 3 parts by weight of about 95 to 100 % strength sulfuric acid per part by weight of N-(2-hydroxyethyl)piperazine and oleum or chlorosulfonic acid at temperatures of about 80° C. to about 250° C., introducing the sulfation mixture formed into about 2.0 to about 6.0 parts by weight of methanol or ethanol per part by weight of N-(2-hydroxyethyl)piperazine at a temperature not to exceed 45° C., the methanol or ethanol having a water content of about 10 to about 30% and isolating the N-(2-sulfatoethyl)piperazine sulfate formed.

3. The process as claimed in claim 2, wherein the reaction is carried out at temperatures of about 100° to 170° C.

4. The process as claimed in claim 2, wherein the reaction is carried out in about 1.3 to about 1.7 parts by weight of 100% strength sulfuric acid per part by weight of N-(2-hydroxyethyl)piperazine.

5. The process as claimed in claim 2, wherein the mixture is of 100% sulfuric acid and oleum, and the oleum has a sulfur trioxide content of about 0.3 to about 0.8 part by weight per part by weight of N-(2-hydroxyethyl)piperazine.

6. The process as claimed in claim 2, wherein the mixture is of 100% sulfuric acid and oleum, and the oleum has a sulfur trioxide content of about 0.4 to about 0.7 part by weight per part by weight of N-(2-hydroxyethyl)piperazine.

7. The process as claimed in claim 2, wherein the mixture is of 100% sulfuric acid and oleum, and the oleum has a sulfur trioxide content of about 0.55 to about 0.65 part by weight per part by weight of N-(2-hydroxyethyl)piperazine.

8. The process as claimed in claim 2, wherein the mixture is of relatively highly concentrated sulfuric acid and chlorosulfonic acid, and said chlorosulfonic acid is present in an amount from about 0.6 to about 1.3 parts by weight per part by weight of N-(2-hydroxyethyl)piperazine.

9. The process as claimed in claim 2, wherein the mixture is of relatively highly concentrated sulfuric acid and chlorosulfonic acid, and said chlorosulfonic acid is present in an amount from about 0.7 to about 1.0 part by weight per part by weight of N-(2-hydroxyethyl)piperazine.

10. The process as claimed in claim 2, wherein the mixture is of relatively highly concentrated sulfuric acid and chlorosulfonic acid, and said chlorosulfonic acid is present in an amount from about 0.80 to about 0.95 part by weight per part by weight of N-(2-hydroxyethyl)piperazine.

11. The process as claimed in claim 2, wherein the sulfation mixture formed is introduced into about 3.0 to about 5.0 parts by weight of methanol or ethanol per part by weight of N-(2-hydroxyethyl)piperazine.

12. The process as claimed in claim 2, wherein the sulfation mixture formed is introduced into about 3.2 to about 3.8 parts by weight of methanol or ethanol per part by weight of N-(2-hydroxyethyl)piperazine.

13. The process as claimed in claim 2, wherein the sulfation mixture is introduced into methanol or ethanol having a water content of about 15 to about 25% by weight.

14. The process as claimed in claim 2, wherein N-(2- sulfatoethyl) piperazine sulfate seed crystals are added to the sulfation mixture.

15. The process as claimed in claim 2, wherein, after the N-(2-sulfatoethyl)piperazine sulfate formed has been isolated, the alcohol obtained, which contains sulfuric acid, is recovered by distillation and used in a subsequent batch.

16. The process as claimed in claim 2, wherein said process consists essentially of reacting N-(2-hydroxyethyl)piperazine in a mixture of about 0.8 to about 3 parts by weight of about 95 to 100 % strength sulfuric acid per part by weight of N-(2-hydroxyethyl)piperazine and oleum or chlorosulfonic acid at temperatures of about 80° C. to about 250° C., introducing the sulfation mixture formed into about 2.0 to about 6.0 parts by weight of methanol or ethanol per part by weight of N-(2-hydroxyethyl)piperazine, at a temperature not to exceed 45° C., the methanol or ethanol having a water content of about 10 to about 30% and isolating the N-(2-sulfatoethyl)piperazine sulfate formed.

17. The process as claimed in claim 16, wherein said process consists of reacting N-(2-hydroxyethyl)piperazine in a mixture of about 0.8 to about 3 parts by weight of about 95 to 100 % strength sulfuric acid per part by weight of N-(2-hydroxyethyl)piperazine and oleum or chlorosulfonic acid at temperatures of about 80° C. to about 250° C., introducing the sulfation mixture formed into about 2.0 to about 6.0 parts by weight of methanol or ethanol per part by weight of N-(2-hydroxyethyl)piperazine, at a temperature not to exceed 45° C., the methanol or ethanol having a water content of about 10 to about 30% and isolating the N-(2-sulfatoethyl)piperazine sulfate formed.

\* \* \* \* \*